United States Patent [19]
Enstrom

[11] Patent Number: 4,738,261
[45] Date of Patent: Apr. 19, 1988

[54] MEDICAL LANCET MEANS

[76] Inventor: Hans Enstrom, Graners Grand 1, S-151 57 Sodertalje, Sweden

[21] Appl. No.: 920,832

[22] Filed: Oct. 17, 1986

Related U.S. Application Data

[63] Continuation-in-part of Ser. No. 541,989, Oct. 14, 1983, Pat. No. 4,676,244, which is a continuation-in-part of Ser. No. 245,080, Mar. 18, 1981, abandoned.

[30] Foreign Application Priority Data

Apr. 23, 1980 [SE] Sweden .................... 8003057

[51] Int. Cl.⁴ .............................. A61B 17/32
[52] U.S. Cl. ................................ 128/314
[58] Field of Search .......... 128/329 R, 330, 314, 128/315; 604/156, 157, 144

[56] References Cited

U.S. PATENT DOCUMENTS

| | | | |
|---|---|---|---|
| 2,442,416 | 6/1948 | Kulicke et al. | 128/314 |
| 3,358,689 | 12/1967 | Higgins | 128/329 P |
| 3,760,809 | 9/1973 | Campbell | 128/314 |
| 3,815,604 | 6/1974 | O'Malley et al. | 128/305 X |
| 4,164,224 | 8/1979 | Hastings | 128/330 |

FOREIGN PATENT DOCUMENTS

| | | | |
|---|---|---|---|
| 188439 | 1/1957 | Austria | 128/314 |
| 2074453 | 10/1981 | United Kingdom | 128/314 |

*Primary Examiner*—Michael H. Thaler
*Attorney, Agent, or Firm*—Murray Schaffer

[57] ABSTRACT

A plunger, having an oblong body with a front end and a rear end and a lancet having a pointed end section projecting axially from said body at the front end, is insertable in a cylinder having an oblong hollow body with a front end, a rear end and an axial hole. The cylinder is at least elastically distendible in the radial direction adjacent its rear end. The plunger is of such a length and the lancet is so arranged that the pointed end section of the lancet protrudes a predetermined distance out of the cylinder at the front end when the plunger is fully inserted in the cylinder thereby defining an operative puncturing position. The plunger and cylinder have a first engaging stop arranged after partial insertion of the plunger, to temporarily prevent continued insertion at a predetermined initial position. The arresting function of the stop is overcome by applying pressure on the plunger thereby radially distending the cylinder and allowing the plunger to be pushed the remaining distance into the cylinder from the initial position to the operative position.

7 Claims, 1 Drawing Sheet

MEDICAL LANCET MEANS

RELATED APPLICATION

This patent application is a continuation-in-part of copending application Ser. No. 541,989 filed Oct. 14, 1983, now U.S. Pat. No. 4,676,244 which was a Continuation-in-Part of Ser. No. 245,080 filed Mar. 18, 1981, now abandoned.

BACKGROUND OF THE INVENTION

The present invention relates to an improved medical lancet means for effecting bleeding by puncturing the skin of an individual to permit the collection of a drop of blood for diagnostic purposes or similar medical use.

It is known to puncture the skin with a lancet retaining body which is used in combination with a separate mechanical apparatus including a biased striker mechanism and a device to release the striker. The striker mechanism has a support for mounting a lancet retaining body therein. Such an apparatus is expensive in manufacture and time-consuming in use. When the lancet is mounted in the support there is the danger of the sterile lancet being accidentally touched with the fingers or other objects with consequent danger of bacterial contamination of the lancet. Neither is it possible to make the lancet tip invisible to the patient.

It is, therefore, an object of the present invention to provide an improved medical lancet means which can be produced more economically and which can be used more conveniently and safely than previously designed lancets.

It is a further object of the present invention to provide a medical lancet means which does not require packaging in a separate wrapper in order to insure the sterility thereof and which makes use of all members thereof for the incision including the member that protects the lancet tip.

These and other objects of this invention will become apparent from the detailed description and the claims to follow when read in conjunction with the accompanying drawings.

DESCRIPTION OF THE INVENTION

Figure 1:
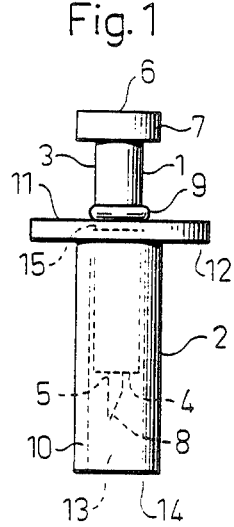
FIG. 1 is a side view of a medical lancet means according to one embodiment of the invention in initial position.

The improved medical lancet means shown in the drawings comprises two cooperating members in the form of a male member 1 and a female member 2, both of which preferably being disposable.

The male member comprises an oblong solid, cylindrical rod body 3 and a lancet 5 of suitable metal projecting axially from the front end 4 of the rod body. It also comprises a circular pressure plate 7 formed at the rear end 6 of the rod body. The rod body and the pressure plate are manufactured of suitable plastic material in one piece, the lancet being molded into the body at the same time so that it is permanently fixed in the solid rod body and so that a pointed end section 8 thereof projects axially therefrom. Furthermore, the male member 1 carrying the lancet is provided with a circumferential ridge 9 or the like protrusion to termporarily obstruct movement, or some other temporary stop means, the function of which will be explained below.

The female member acting as carrier and guide for the male member comprises an oblong, sleeve-like, open-ended, cylindrical hollow body 10 and a finger-grip plate 12 formed at the rear end 11 of the body. In the embodiment shown, the body 10 has an axial through-hole 13 adapted to slidingly receive the rod body 3 of the male member without friction. A slight clearance may be permitted between the parts. The male and female members are so designed with respect to each other that when the male member is fully inserted in the female member the pointed end section 8 of the lancet will project a predetermined distance, usually about 0.5–2 mm, out of the female member. In this final and puncturing operative position the pressure plate 7 is in contact with the finger grip plate 12 or rear end 11. The female member is manufactured of suitable plastic material, preferably of the same plastic material as the male member. However, because the body 10 of the female member is a relatively thin walled sleeve, the body 10 has a degree of radial elasticity not found in the male member.

Figure 2:
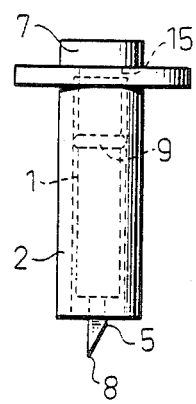
FIG. 2 is a side view of the means according to FIG. 1 in operative position when in use.

The cooperating male and female members 1 are also provided with first engaging stop means adapted to constrict passage or temporarily obstruct their relative movement. The stop means comprises a first element arranged on the rod body of the male member 1 at a predetermined distance from the pointed end section 8 of the lancet, and a second element arranged on the female member at a predetermined distance from the front end 14 thereof to engage with the first element. In the embodiment shown in FIGS. 1 to 5, the first element consists of a radially protruding ridge 9, while the second element consists of a corresponding annular radially inwardly extending ridge 15 on the inner wall or at the entry of the hole in the female member. The ridge 15 of the female member thus forms a constriction of the hole 13 at the entry thereof so that continued movement of the male member 1 into the female member 2 is prevented, as is illustrated in FIG. 1, since the ridge 9 engages the protrusion 15 of the female member. By increasing the pressure with the thumb or other finger on the pressure plate 7 of the male member, the engaging ridges 9 and 15 cooperate with each other to cause the hollow body 10 of the female member 2 to distend radially outward due to the elastic nature of the material and the thinness of the sleeve from which the body 10 is formed. The stop formed by the engaging ridges 9 and 15 is ultimately overcome so that the male member 1 can be pushed the full length, determined by the rod body 3, into the female member, as is illustrated in FIG. 2. When this increased pressure is suddenly released by the movement of the ridges 9 past and out of engagement with the ridge 15, the male member 1 acquires an extremely high speed during its further movement the rest of the distance into the female member 2 until a second engaging stop means is reached, comprising the pressure plate 7 of the male member and the rear end 11 of the female member. This in turn means that the pointed end 8 of the lancet is pushed out of the female member at a correspondingly high speed, rapidly penetrating the skin and the blood vessels beneath. It will be understood that the front end 14 of the female member will be in contact with the skin at least from the point when the pressure is increased on the male member after the temporary engagement of the first stop means has been reached.

Since the lancet 8 acquires a high speed upon the sudden release of the first stop means and pushing in of the male member, the pointed end section of the lancet will penetrate the skin extremely quickly. It has been found that, thanks to this, the sensation of pain is extremely slight and brief.

The ridge 9 on the male member is placed at a specific point on the rod body 3 so that the distance between the ridge 9 and the pointed end section 8 of the lancet is the same as and preferably slightly less than the distance between the front end 14 of the female member and the stop ridge 15. It is thus ensured that the pointed end section 8 of the lancet will not be visible from the side when the first stop means is temporarily in engagement, provided the female member 2 is made of opague plastic, which is preferred. It is believed that it is of great psychological significance for many patients that the lancet is invisible.

Figure 3:
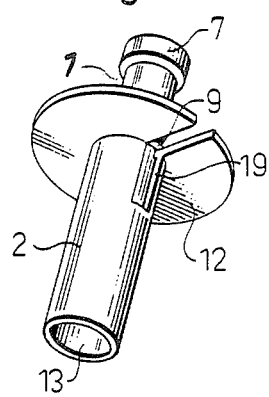
FIG. 3 is a perspective view of a modified embodiment of the means according to the invention.

If desired, the female member may be provided with a slit 19 at its rear end 11, to enable the entry portion of the hole 13 to more readily distend by expansion upon application of said pressure on the male member. Such an embodiment is illustrated in FIG. 3.

Figure 4:
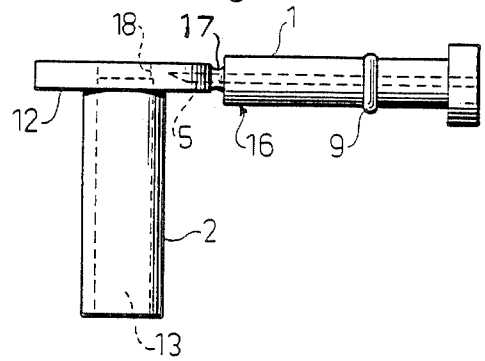
FIGS. 4 and 5 are a side view and top view, respectively, of another embodiment of a means according to the invention produced as a unit with the lancet unexposed and sterile, but having members which can be separated.
Figure 5:
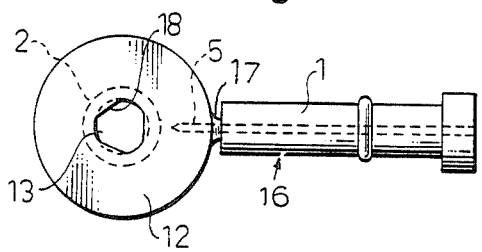

The medical lancet means can preferably be made in one piece, the male member and female member being in an integral piece or unit 16 and easily severable from each other at the moment of use. Such a unit is shown in FIGS. 4 and 5. The unit is injection molded so that the pointed end section of the lancet is located in the finger-grip plate 12 of the female member and directed radially therein. A slight twist of the male member will separate this from the female member at the thin and frangible connection 17 which surrounds a small portion of the lancet with the lancet being molded in this manner, it is completely protected and sterile up to the moment of use and, moreover, by an operative member, i.e. the female member, of the medical lancet means. Thus, no special protection element which must then be disposed is required for the lancet. In the embodiment according to FIGS. 4 and 5, the female member has been provided with three evenly distributed ridges or protrusions 18 cooperating with the protrusion 9 of the male member to form said first stop means.

Instead of placing the male and female members in right angle, as shown in FIG. 4, they may be molded to form an oblong unit, the pointed end section of the lancet being enclosed in the finger-grip plate 123 from above and, if necessary, in extra material under the plate.

The plastic material used for the medical lancet means is entirely free from foreign substances and is of a quality approved for foodstuffs. Thus, plasticized organic polymeric compositions, such as a polyvinyl chloride, polyethylene, polypropylene, and the like plastic materials, are well suited for molding the medical lancet means. The lancet is made of special stainless steel.

By means of a special technique, it has been found unnecessary to provide the lancet with any grindings, such as grooves or external attachment means which are normal for the attachment of a lancet or other steel object in a plastic body. This new technique entails washing the lancet with alcohol or alcohol solution prior to its automatic insertion in the plastic injection molding tool, without any object with fat or oily surface coming into contact with the lancet after washing.

To ensure secure accurate molding of the lancet into the male member, the injection molding tool may comprise three radially directed holder elements which support the automatically inserted lancet from two opposite directions, such as from below and above, corresponding radial slits being formed in the molded male member.

The stop means which act last, i.e., said second stop means which are formed in the embodiment shown by the pressure plate 7 of the male member and the rear end 11 of the female member, according to an alternative embodiment may be formed by the front end 4 of the male member and an inner shoulder or ridge in the female member, said shoulder or ridge being formed by a bottom section in the female member, the hole thereof terminating at a distance from the front end of the female member. A narrow central hole is made in said bottom section for passage of the pointed end of the lancet.

Figure 6:
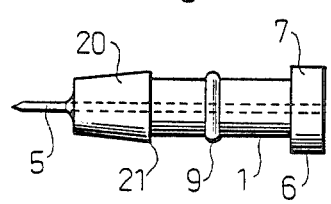
FIG. 6 is a side view of another embodiment of a plunger according to the present invention.

According to a further embodiment, shown in FIG. 6, the male member is provided with a device which prevents the male member from falling out of the female member when the medical lancet means is in its initial position prepared for use. In this device the plunger 1 is provided with a conical forward end 20 which is enlarged at its rear so that it forms a circumferential protrusion 21. This protrusion 21 is arranged to engage with either the annular ridge 15 or the three separate ridges 18 of the hole of the female member 2 after the partial insertion of the plunger 1 into the cylinder. The diameter of the protrusion 21 is smaller than that of the ridge 9 but greater than the ridges 15 or 18. Thus, the protrusion 21 forms a further stop means which prevents the plunger and lancet from accidentally falling out of the rear end of the cylinder hole 3 and thereby ensures the sterility of the lancet once it has been removed from its sterile position and made ready for use. A ridge, step or similar stop means may be formed on rod body 3 between front end 4 and ridge 9 in view of the circular protrusion.

As mentioned, the lancet may consist of a suitable metal. However, it may of course consist of some other suitable material if desired. The lancet may, for instance, consist of a suitable plastic material and according to such an embodiment the lancet is molded as an integral part of the male member, i.e., of the same plastic material.

What is claimed is:

1. A disposable miniature medical lancet for obtaining a drop of blood by puncturing the skin without passing through the body comprising a cylinder and a plunger, said cylinder consisting of a sleeve axially open at the front and rear ends and being elastically distensible in the radial direction under force applied thereto, said plunger being insertable at its front end into said cylinder, said plunger and said cylinder having a slight clearance enabling said plunger to be normally freely slidable within said cylinder, said plunger having a radially extending flange at its rear end engageable with the rear end of said cylinder for limiting passage of said plunger through said cylinder and defining the full insertion of said plunger in said cylinder, a lancet integrally formed with said plunger and having a pointed end projecting axially from said front end of said plunger, said plunger, cylinder and lancet being so formed that said lancet protrudes from the front end of said cylinder a predetermined distance when said plunger is fully inserted within said cylinder, the outer surface of said plunger having a radially outwardly protruding peripheral ridge spaced from the rear end thereof and the inner surface of said cylinder having at least one radial projection extending inwardly from the wall adjacent the rear end thereof, said peripheral ridge and radial projection co-operating to form detent means temporarily restricting the freely slidable movement of said plunger at a predetermined location within said cylinder, said location being less than the full insertion of said plunger so that said lancet remains within said cylinder spaced from the front end thereof, said restriction being overcome by application of an axial force on said plunger at said rear end thereof, said axial force causing said cylinder to elastically distend in the radial direction permitting the peripheral ridge to pass axially beyond said projection without fracture of said ridge or projection, said plunger being thereafter freely movable through said cylinder rapidly into the fully inserted position.

2. A medical lancet according to claim 1, wherein the cylinder is formed with a radially exterior flange forming finger-grip for the user.

3. The lancet according to claim 1, wherein said lancet protrudes from the front end of said plunger, when fully inserted in said cylinder between 0.5-2 mm.

4. A disposable miniature medical lancet for obtaining a drop of blood by puncturing the skin without passing through the body comprising a cylinder and a plunger, at least said cylinder being elastically distensible in the radial direction under force applied thereto, said plunger being insertable at its front end into said cylinder, said plunger and said cylinder having a slight clearance enabling said plunger to be normally freely slidable within said cylinder, said plunger having a radially extending flange at its rear end engageable with the rear end of said cylinder for limiting passage of said plunger through said cylinder and defining the full insertion of said plunger in said cylinder, a lancet integrally formed with said plunger and having a pointed end projecting axially from said front end of said plunger, said plunger and cylinder being molded as a unit, said plunger being integrally connected at its forward end to a portion of said cylinder with the lancet enbedded therein, said connection being thin and easily frangible permitting severance of said plunger from said cylinder and exposure of the tip of said lancet, said plunger, cylinder and lancet being so formed that said lancet protrudes from the front end of said cylinder a predetermined distance when said plunger is fully inserted within said cylinder, the outer surface of said plunger having a radially outwardly protruding peripheral ridge spaced from the rear end thereof and the inner surface of said cylinder having at least one radial projection extending inwardly from the wall adjacent the rear end thereof, said peripheral ridge and radial projection cooperating to form detent means temporarily restricting the freely slidable movement of said plunger at a predetermined location within said cylinder, said location being less than the full insertion of said plunger so that said lancet remains within said cylinder spaced from the front end thereof, said restriction being overcome by application of an axial force on said plunger at said rear end thereof, said axial force causing said cylinder to elastically distend in the radial direction permitting the peripheral ridge to pass axially beyond said projection without fracture of said ridge or projection, said plunger being thereafter freely movable through said cylinder rapidly into the fully inserted position.

5. A disposable miniature medical lancet for obtaining a drop of blood by puncturing the skin without passing through the body comprising a cylinder and a plunger, at least said cylinder being elastically distensible in the radial direction under force applied thereto, said plunger being insertable at its front end into said cylinder, said plunger and said cylinder having a slight clearance enabling said plunger to be normally freely slidable within said cylinder, said plunger having a radially extending flange at its rear end engageable with the rear end of said cylinder for limiting passage of said plunger through said cylinder and defining the full insertion of said plunger in said cylinder, a lancet integrally formed with said plunger and having a pointed end projecting axially from said front end of said plunger, said plunger, cylinder and lancet being so formed that said lancet protrudes from the front end of said cylinder a predetermined distance when said plunger is fully inserted within said cylinder, the outer surface of said plunger having a circumferential protrusion adjacent its front end and the inner surface of said cylinder having at least one radial projection extending inwardly from the wall adjacent the rear end thereof, said circumferential protrusion and radial projection cooperating to form unidirectional detent means permitting the insertion of at least the front end of said plunger in said cylinder and preventing the withdrawal of said cylinder therefrom, said plunger having a radially outwardly protruding peripheral ridge formed between the circumferential protrusion and the radially extending flange for temporarily restricting the freely slidable movement of said plunger after insertion of the front end at a predetermined location within said cylinder, said location being less than the full insertion of said plunger so that said lancet is arrested within said cylinder spaced from the front end thereof, said restriction being overcome by application of an axial force on said plunger at said rear end thereof, said axial force causing said cylinder to elastically distend in the radial direction permitting the peripheral ridge to pass axially beyond said projection without fracture of said ridge or projection, said plunger being thereafter freely movable through said cylinder rapidly into the fully inserted position.

6. The lancet according to claim 5 wherein the front end of said plunger is in the shape of a truncated cone, the larger base being spaced from the front end of the plunger and be radially extended to form the circumferential protrusion.

7. The lancet according to claim 6 wherein said circumferential ridge has a diameter less than that of said peripheral ridge of said plunger but greater than that of the entrance to said cylinder at the rear end.

* * * * *